United States Patent [19]

Crivello et al.

[11] Patent Number: 4,864,054

[45] Date of Patent: Sep. 5, 1989

[54] METHOD FOR MAKING CATIONICALLY POLYMERIZABLE AROMATIC POLYPROPENYL ETHERS

[75] Inventors: James V. Crivello, Clifton Park; David A. Conlon, Schenectady, both of N.Y.

[73] Assignee: General Electric Company, Schenectady, N.Y.

[21] Appl. No.: 490,924

[22] Filed: May 2, 1983

[51] Int. Cl.[4] .................. C07C 67/03; C07C 41/06; C07C 41/32

[52] U.S. Cl. ..................... 560/64; 560/80; 560/89; 568/627; 568/643; 568/654

[58] Field of Search .............. 560/64, 89; 568/643, 568/654, 627, 608, 609, 606

[56] References Cited

U.S. PATENT DOCUMENTS

| | | | |
|---|---|---|---|
| 2,874,141 | 2/1959 | Christenson et al. | 568/654 X |
| 3,057,909 | 10/1962 | Sebelist et al. | 560/91 X |
| 3,288,842 | 11/1966 | Verdol | 560/91 X |
| 4,017,549 | 4/1977 | Karrer et al. | 568/640 |
| 4,388,450 | 6/1983 | Crivello | 568/640 X |

FOREIGN PATENT DOCUMENTS

234389 2/1960 Australia.

OTHER PUBLICATIONS

Chemical Abstracts, vol. 82, 74549a, (1975).
Isomerization of Estragole to Anethole, Pasquale, Synthetic Communications, 10(3), 225–231, (1980).
Communications to the Editor, Hubert, Jul. 1968, Chemistry and Industry, p. 975.
Chemistry of the Metal Carbonyls, Part XXXII. Isomerization of Allyl Compounds and the Dimerisation of Norbornadiene, Jolly et al, JCS, (1965), pp. 6416–6420.
Isomerisation of Allyl Phenyl Ethers and Allylphenols with Transition Metal Catalysts, Golborn et al, JCS Perkin I, (1973), pp. 2870–2875.
The Rearrangement of Allyl Ethers to Propenyl Ethers, Prosser, JACS 83, 1701–1704, (1961).
Etude des isomerisations sous L'influence des bases en milieu aprotique, Caubere et al, Bull. Soc. Chim. Fr., 459, (1968).
Cleavage Reaction of 2-Butenyloxy Derivatives with Potassium t-Butoxide, Kesslin et al, J. of Org. Chem., 31, 2682–2684, (1966).
Selective Cleavage of Allyl Ethers under Mild Conditions by Transition Metal Reagents, Corey et al, J. of Org. Chem., vol. 38, No. 18 (1973), p. 3224.
The Allyl Ether as a Protecting Group in Carbohydrate Chemistry, Cunningham et al, Tetrahedron Letters, No. 19, pp. 1191–1196, (1964) Pergamon Press Ltd., Great Britain.
The Base-Catalyzed Isomerization of Allyl to Propenyl Amines, Price et al, Tetrahedron Letters No. 2, pp. 69–73, (1962), Pergamon Press Ltd., Great Britain.
Base-Catalysed Prototropic Rearrangement. Part I, Comparison of the Base-Catalysed and the Metal Carbonyl-Catalysed Isomerisation of Allyl Ethers, Hubert et al, JCS Perkin 11, (1972), pp. 366–370.
Isomerization of Allyl Alcohols by a Water Soluble Ruthenium Catalyst in a Two-Liquid Phase System, Sasson et al, J. of Molecular Catalysis, 6, (1979), 289–292.
Isomerization of Allyl Ethers Catalysed by the Cationic Iridium Complex ]IR(cyclo-octa-1,5-diene) (PMePH$_2$)$_2$]PF$_6$. A Highly Stereoselective Route to Trans-Propenyl Ethers, Baudry et al, JCS Chem. Comm., (1978), pp. 694–695.
Isomerization of N-Allylamides and –imides to Aliphaitc Anamides by Iron, Rhodium, and Ruthenium Complexes, Stille et al, J. Org. Chem. (1980), 45, 2139–2145.
Hydroxide Ion Initiated Reactions in Phase Transfer Catalysis. I. Isomerization of Allylbenzene, Halpern, Tetrahedron Letters, vol. 22, pp. 703–704, Pergamon Press Ltd., (1981), Great Britain.
Novel Preparation of Silyl Enol Ethers from Allyl Alcohols, Suzuki et al, Tetrahedron Letters, No. 16, pp. 1415–1418, Pergamon Press Ltd., (1979), Great Britain.
Solvent Effects in the Base-Catalyzed Isomerization of Allyl to Propenyl Ethers, Price et al, J.A.C.S. 83, 1773, (1961).
Chemistry of Metal Hydrides. XV. Mechanism of Double-Bond Migration Induced by Platinum(II) Hydrides, Inorganic Chemistry, vol. 12, No. 7, (1973), pp. 1566–1570.

*Primary Examiner*—Werren B. Lone
*Assistant Examiner*—Vera C. Clarke
*Attorney, Agent, or Firm*—William A. Teoli; James C. Davis, Jr.; William H. Pittman

[57] ABSTRACT

A method is provided for making cationically polymerizable aromatic polypropenylethers and to the aromatic polypropenylethers made thereby. Aromatic polyalkylene glycol prepared from the corresponding polyphenol is reacted with an allylhalide to produce aromatic polyallylether which is thereafter isoemrized to the corresponding cationically polymerizable aromatic polypropenylether.

4 Claims, No Drawings

4,864,054

METHOD FOR MAKING CATIONICALLY POLYMERIZABLE AROMATIC POLYPROPENYL ETHERS

CROSS REFERENCE TO RELATED APPLICATIONS

Reference is made to copending applications of James V. Crivello, Ser. No. 243,302, filed Mar. 13, 1981, for Aromatic Polyvinylethers and Heat Curable Molding Compositions Obtained Therefrom, now U.S. Pat. No. 4,388,450, Ser. No. 459,442, filed Jan. 20, 1983, for Aromatic Polyvinylethers and Heat Curable Molding Compositions Obtained Therefrom, now U.S. Pat. No. 4,518,788, and to our application Ser. No. 293,303, filed Mar. 13, 1981, now abandoned, for Condensation Method for Making Aromatic Polyvinylethers, where the aforementioned applications are assigned to the same assignee as the present invention and incorporated herein by reference.

BACKGROUND OF THE INVENTION

Prior to the present invention, it was observed that alkenyl unsaturated aromatic ethers underwent rearrangement to low molecular weight poly alkenyl phenols when attempts were made to cationically polymerize such aryl alkenyl ethers as shown by the following equation:

$$nCH_2=CH + R^+ \longrightarrow R(CH_2-CH)_{\overline{n}}$$

(with phenyl-O and phenyl-OH groups)

where $R^+$ is a cationic polymerization catalyst.

As shown in the copending application of James V. Crivello Ser. No. 243,302, certain aromatic polyvinylethers were found to be cationically polymerizable without such rearrangement occurring Experience has shown that in order to successfully cationically polymerize aryl alkenyl ethers, it is necessary to have a protective alkylene radical between the aromatic nuclear oxygen atom and the alkenyloxy radical. Attempts to cationically polymerize aromatic polyallylethers of the formula, $$R^1[GR^2OCHR^3-CR^4=C(R^5)_2]_n \qquad (1)$$

where G is a member selected from the class consisting of $$-O-, -CO-, \text{ and } S,$$

$R^1$ is a polyvalent aromatic radical, $R^2$ is a $C_{(1-8)}$ alkylene radical, $R^3$, $R^4$ and $R^5$ are the same or different monovalent radicals selected from hydrogen, halogen and $C_{(1-8)}$ alkyl radicals and $R^3$ and one of the $R^5$ radical can be divalent $C_{(1-3)}$ alkylene radicals which together can be part of a $C_{(5-8)}$ cycloaliphatic structure, and n is an integer equal to 2 to 10 inclusive, were unsuccessful even though these polyallylethers are insulated from the polyvalent aromatic nucleus $R^1$ through the alkylene radical $R^2$. Journal of Organic Chemistry, 42 (21), 3360, (1977) that monofunctional allylethers can be isomerized to propenylethers using a ruthenium catalyst, such as $RuCl_2(PC_6H_5)_3$. We have discovered that aromatic polyallylethers of formula (1) can be isomerized to produce the corresponding aromatic polypropenylethers of the formula, $$R^1[GR^2OCR^3=CR^4-CH(R^5)_2]_n \qquad (2)$$

where $R^1$, $R^2$, $R^3$, $R^4$, $R^5$, G and n are as previously defined, which can be satisfactorily cationically polymerized.

STATEMENT OF THE INVENTION

There is provided by the present invention, a method for making cationically polymerizable polypropenylethers of the formula, $$R^1[OR^2OCR^3=CR^4-CH(R^5)_2]_n \qquad (3)$$

which comprises, (A) effecting reaction between an aromatic polyalkyleneglycol of the formula $$R^1[OR^2OH]_n \qquad (4)$$

and an allylhalide of the formula, $$C(R^5)_2=CR^4-CH(R^3)X \qquad (5)$$

in the presence of an acid acceptor to produce an aromatic polyallylether, (B) recovering the resulting aromatic polyallylether from the mixture of (A), and (C) heating the aromatic polyallylether of (B) in the presence of an effective amount of an isomerization catalyst to produce the desired cationically polymerizable polypropenylether, where $R^1$-$R^5$ and n are as previously defined and X is a halogen radical.

Radicals included within $R^1$ of formula (1) are, for example, phenylene, tolylene, xylylene, naphthalene, xenyl, anthrylene, biphenylene (structure: two phenylene rings connected by Z)

where Z is selected from $$-O-, -S-, -\overset{O}{\underset{\|}{S}}-, -\overset{O}{\underset{\|}{C}}-, -\overset{O}{\underset{\overset{\|}{O}}{S}}-, \text{ and } -CH_{2y}-$$

(cycloaliphatic C structures shown)

y is equal to 0 to 5 inclusive, and n is as previously defined, and polyvalent aromatic radicals, for example,

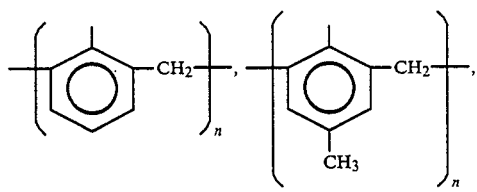

etc., $-(CH_2-CH)_n^-$

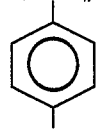

halogenated derivatives thereof are also included, for example, chlorophenylene, bromotolylene, etc. In particular instances, the $R^1$ radicals can be further substituted with $C_{(1-4)}$ alkyl radicals, and mixtures of halogen and alkyl radicals, etc.

Radicals which are included within the definition of $R^2$ are $C_{(1-8)}$ alkylene radicals, for example, methylene, ethylene, trimethylene, tetramethylene, etc. Radicals included within the definition of $R^3$, $R^4$ and $R^5$ are, for example, methyl, ethyl, methylene, ethylene, trimethylene, etc. Radicals included within the definition of $R^3$, $R^4$ and $R^5$ are, for example, hydrogen, $C_{(1-8)}$ monovalent alkyl radicals, such as methyl, ethyl, propyl, etc., and halogen radicals, for example, chloro, bromo, etc.

There are included within the aromatic polypropenylethers of formula (3), compounds such as

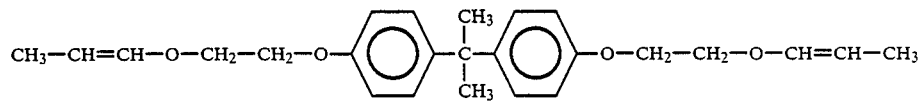

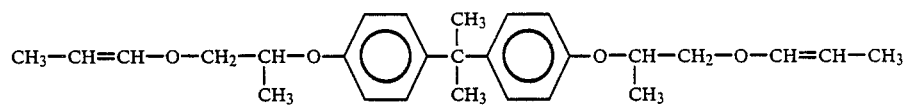

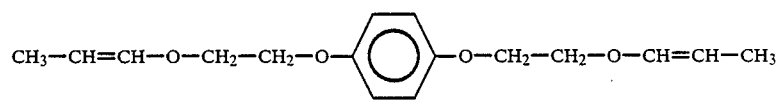

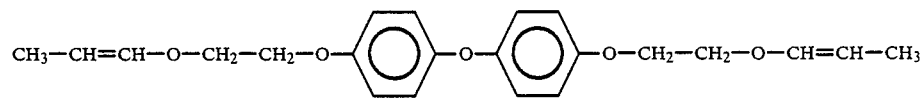

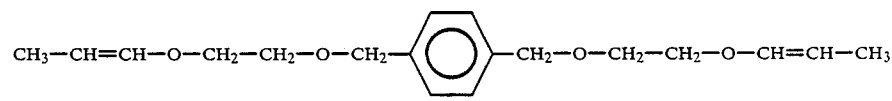

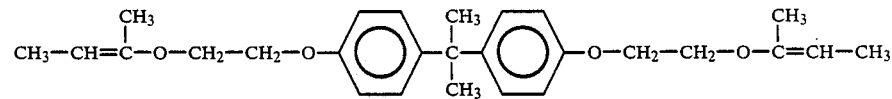

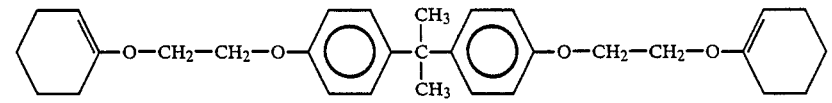

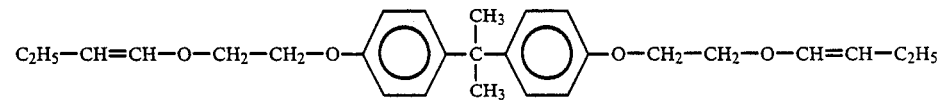

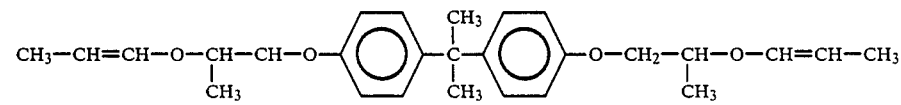

-continued

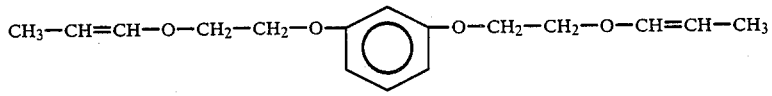

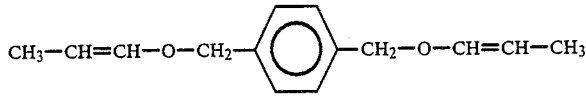

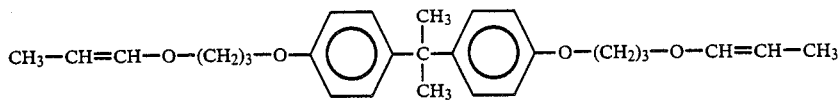

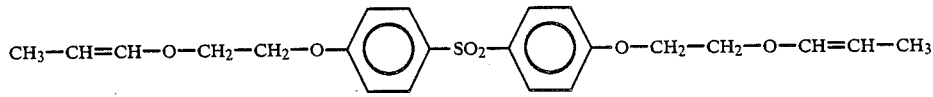

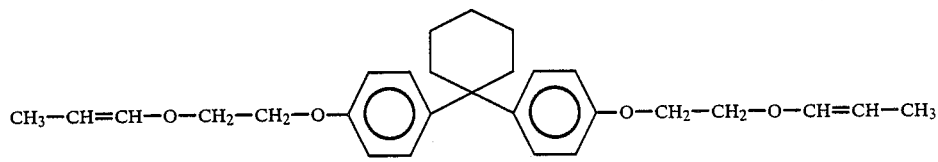

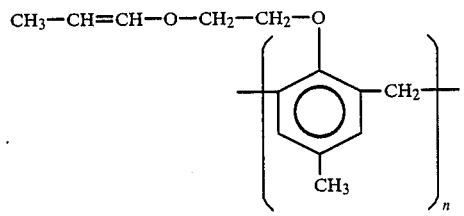

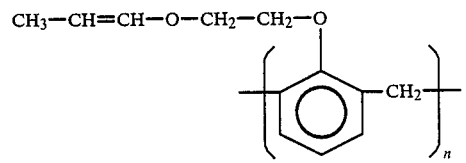

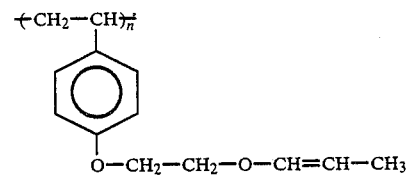

Among the methods for making the aromatic polyglycols of formula (4) are, for example, effecting reaction between an aromatic polyphenol and an alkylene oxide in the presence of a tertiary amine catalyst. Reaction between allylhalide and an appropriate aromatic polyphenol in the presence of an acid acceptor, such as an alkali metal hydroxide, for example, sodium hydroxide, will provide some of the aromatic polyallylether included within formula (1).

An additional procedure which can be used to make some of the aromatic polyallylethers of formula (1), is the employment of polyfunctional aromatic esters of the formula,

where m is an integer having a value of from 2 to 4 inclusive, $R^6$ is a $C_{(1-8)}$ alkyl radical, which can be reacted with an appropriate allylether of an alkylene glycol of the formula,

where $R^2$, $R^3$, $R^4$ and $R^5$ are as previously defined, to effect an ester interchange with the above aromatic polyester.

Some of the aromatic polyphenols which can be used to make the aromatic polyglycols of formula (4) are, for example,
2,2-bis(4-hydroxyphenyl)propane (bisphenol-A);
2,4'-dihydroxydiphenylmethane;
bis-(2-hydroxyphenyl)methane;
1,1-bis-(4-hydroxyphenyl)ethane;
1,1-bis-(4-hydroxyphenyl)propane;
3,3-bis-(4-hydroxyphenyl)pentane;
4,4'-dihydroxybiphenyl;
4,4'-dihydroxy-3,3'5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenylsulfoxide;
4,4'-dihydroxydiphenylsulfide;
hydroquinone;
catechol;
resorcinol;
2,2-bis(3,5-dibromo-4-hydroxyphenyl)propane;
3,3-bis(4-hydroxyphenyl)fluorene;
3,4'-dihydroxydiphenylmethane;
4,4'-dihydroxybenzophenone;
4,4'-dihydroxydiphenylether;
1,1-dichloro-2,2-bis(4-hydroxyphenyl)ethylene;
1,1,1-trichloro-2,2-bis(4-hydroxyphenyl)ethane;
4-hydroxybenzoic acid, etc.

Allylhalides included within formula (5) are, for example, allylchloride, allylbromide, crotyl chloride, methallylbromide, 2-cyclohexenylbromide, 2-chloro-3-butene, 3-chloro-1-pentene, allyliodide, etc.

Some of the polyfunctional aromatic ester of formula (6) include
4-hydroxymethylbenzoate;
dimethylterephthalate;
dimethylisophthalate;
diethylphthalate;
methylsalicylate;
diethyl-2,3-naphthalenedicarboxylate;
dimethyl-4,4'-biphenyldicarboxylate;
trimethyltrimelitate;
tetraethylpyromelitate.

In the practice of one form of the invention the aromatic polyallylether of formula (1) can be made by effecting reaction between the aromatic polyalkylene glycol of formula (4) and an appropriate allylhalide of formula (5) in the presence of an acid acceptor at a temperature in the range of from $-10°$ C. to $100°$ C. There can be used as the acid acceptor, alkali metal hydroxide such as sodium hydroxide, potassium hydroxide, or organic amines, for example, triethylamine, tributylamine, benzyldimethylamine, N,N,N',N'-tetramethylethylenediamine, etc., sufficient allylhalide should be used to provide at least a stoichiometric equivalent of halide atoms of the allylhalide and OH of the aromatic polyalkylene glycol. In particular instances, it may be desirable to use an inert organic solvent such as toluene to facilitate recovery of product.

In instances were the aromatic polyallylether is made utilizing an aromatic polyester of formula (6), substantially equivalent molar amounts of an alkylene glycol monoallylether can be used there can be utilized from about titanium compound, for example, titanium tetraisopropoxide, or tin compound such as stannous octoate, etc. Some of these alkylene glycol monoallylethers are, for example, 2-allyloxyethanol, 2-methallyloxyethanol, 3-allyloxy-1-propanol, 2-allyloxy-1-propanol, 4-allyloxy-1-butanol, diethyleneglycolmonoallylether, ethyleneglycolmonocrotylether. Temperatures in the range of between about $50°$ C. to $250°$ C. can be used to effect an ester interchange and the separation of alcohol, such as methanol, ethanol, etc , from the aromatic polyester.

Isomerization of the aromatic polyallylether can be effected at temperatures in the range of from $25°$ C. to $200°$ C. using an effective amount of an isomerization catalyst which can be from 0.01% to 5% by weight based on the weight of the reaction mixture. Some of the isomerization catalysts which can be used are, for example, metallic palladium, platinum or rhodium on carbon, silica, or alumina, tris(triphenylphosphine) ruthenium dichloride, $[Ir(cyclo-octa-1,5-diene)(PCH_3Ph_2)_2]^+PF^-_6$, $PdCl_2(PhCN)_2$, $Fe(CO)_5$, $RhCl(PPh_3)_3$, $H_2Ru(PPh_3)_4$, potassium-t-butoxide, sodium, or potassium amide in liquid ammonia, dispersed on alumina or in hexamethylphosphortriamide.

The aromatic polypropenylethers of the present invention can be combined with an appropriate thermal curing catalyst such as an effective amount of an arylonium salt such as diphenyliodonium hexafluorophosphate, or an organic oxidant as shown in copending application Ser. No. 243,302 and an inactive ingredients such as silica, talc, clay, glass fibers, extenders, hydrated alumina, carbon fibers, process aids, etc., in amounts of up to 500 parts of inactive ingredients per 100 parts of aromatic polyallylether or active hydrogen compound reaction products thereof. The resulting heat curable compositions can be applied to such substrates as metal, rubber, plastic, molded parts of films, paper, wood, glass, cloth, concrete, ceramic, etc.

Some of the applications in which the above described heat curable compositions containing the aromatic polypropenylethers of the present invention can be used are, for example, protective, decorative and insulating coatings, potting compounds, printing inks, sealants, adhesives, molding compounds, wire insulating, textile coatings, laminates, impregnated tapes, varnishes, etc.

In order that those skilled in the art will be better able to practice the invention, the following examples are given by way of illustration and not by way of limitation. All parts are by weight.

EXAMPLE 1

There was added 240 grams (6 moles) of solid sodium hydroxide with stirring to a solution of 632.76 grams (2 moles) of bisethoxylated bisphenol-A, 300 ml of toluene and 459.2 grams (6 moles) of allylchloride. The mixture was stirred for about 30 minutes.

There was then added 32 grams (0.1 mole) of tetrabutylammonium bromide and the mixture was stirred for an additional 0.5 hour. The temperature of the mixture was then slowly raised to $50°$ C. and the external heating was then discontinued. An exothermic reaction occurred and the temperature of the mixture rose to $100°$ C. The temperature of the mixture was reduced to $75°$ C. with the aid of external cooling and the reaction mixture was then stirred for 16 hours.

The reaction mixture was then poured into 2 liters of distilled water and the organic layer was recovered. The organic layer was washed three times with 500 ml of water and dried over solid sodium sulfate. Toluene was then removed under vacuum from the resulting product. There was obtained 690 grams of bisallylether of bisphenol-A. The identity of the product was further confirmed by elemental analysis for $C_{25}H_{32}O_4$ calculated: %C, 75.72; %H, 8.14; %O, 16.14; Found: %C, 75.60; %H, 8.23; %O, 16.03.

There was heated under a nitrogen atmosphere with stirring for 1.5 hours at a temperature which was slowly brought up to 120° C., 396.5 grams (1 mole) of the above bisallylether of bisphenol-A and 0.96 grams ($1 \times 10^{-3}$ mole) of $RuCl_2[P(C_6H_5)_3]$. The product was then allowed to cool and examined by nuclear magnetic resonance. Based on method of preparation, there was obtained a bispropenylether having the formula,

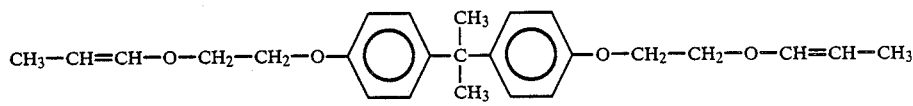

The above product was found to be a mixture of three isomeric isopropenylethers (cis-cis, cis-trans and trans-trans). The identity of the product was further confirmed by its elemental analysis for $C_{25}H_{32}O_4$ (tran-strans isomer) Calculated: %C, 75.72; %H, 8.14; %O, 16.14. Found: %C, 75.96; %H, 8.14; %O, 157.

Ten grams of the above bisisopropenylether (BPADEPE) containing 1% by weight of diphenyliodonium hexafluoroarsenate was placed in a Sunshine Gel timer. The gel time recorded at 100° C. was 38.2 minutes.

A mixture composed of 100 grams of BPADEPE, 2 grams of a 50% solution of diphenyliodonium hexafluoroarsenate in propylene carbonate and 0.3 grams of copper stearate was poured into a ⅛ inch×6 inch×6 inch plate mold preheated to 100° C. The mold was placed into a forced air oven at 100° C. for 0.5 hour. There was obtained a solid plaque upon cooling. Gel time of the above mixture in a sunshine gel timer was found to be 5.4 minutes at 100° C.

A mixture of BPADEPE and diphenyl-4-thiophenoxyphenylsulfonium hexafluorophosphate (1% by weight of the mixture) was spread onto a glass plate as a 1 mil film. The film was irradiated with a GE H3T7 medium pressure mercury arc lamp at a distance of 4 inches from the lamp. A tack-free time of 4 seconds was recorded.

EXAMPLE 2

A mixture of 9 grams of bisallylether of ethoxylated BPA, 100 ml of dimethylsulfoxide and 5 grams of potassium t-butoxide was stirred and heated at 100° C. for 1 hour. The mixture was then allowed to cool to room temperature and poured into water. The resulting product was extracted from the aqueous mixture with diethylether. The diethylether layer was washed with water, dried with anhydrous sodium sulfate and the solvent removed under vacuum. Based on method of preparation, there was obtained a quantitative yield of the bispropenylether of bisphenol-A The identity of the product was further confirmed by NMR.

A mixture of the above BPADEPE and diphenyliodonium hexafluoroarsenate (1% by weight) was irradiated as a 1 mil film in accordance with the procedure of Example 1. There was obtained a tack-free film after 5 seconds exposure. A hard cured 10 mil thick casting was also obtained by adding to the aforementioned mixture 0.25% by weight copper stearate which mixture was heated in a forced air oven at 100° C. for 10 minutes.

EXAMPLE 3

A mixture of 344.43 grams (1 mole) of propoxylated bisphenol-A (Capcure of the Diamond Shamrock Company of Morristown, N.J.), 168.54 grams of KOH and 1.2 liters of dimethylsulfoxide was heated with stirring under nitrogen for 3 hours at 70°-75° C. The heating of the mixture was then discontinued and there was added dropwise 362.94 grams (3 moles) of allylbromide. Upon completion of the reaction the mixture was heated at 65°-75° C. for an additional 2.5 hours. The mixture was allowed to cool and then poured into 2 liters of water. Excess allylbromide was removed from the mixture with nitrogen gas. The organic layer was then separated from the mixture and residual solvents were removed under vacuum. Based on method of preparation there was obtained the bisallylether of propoxylated bisphenol-A having the formula,

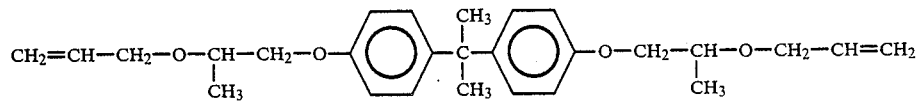

The identity of the above product was further confirmed by NMR.

A mixture of 21.23 grams (0.05 mole) of the above bisallylether of propoxylated bisphenol-A, 224 ml of dimethylsulfoxide and 11.2 grams of potassium-t-butoxide was heated and stirred under a nitrogen atmosphere at 100° C. for 1 hour. The product was then allowed to cool to room temperature and recovered in accordance with the procedure of Example 1. Based on method of preparation there was obtained the bispropenylether of propoxylated bisphenol-A having the formula,

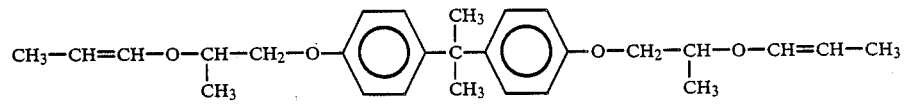

The identity of the product was further confirmed by NMR.

A mixture of 10 grams of the above bispropenylether of propoxylated bisphenol-A and 1% by weight of diphenyliodonium hexafluoroarsenate was found to give a gel time of 19.8 minutes at 125° C. in a Sunshine Gel timer.

EXAMPLE 4

A mixture of 46 grams (0.23 mole) of ethoxylated resorcinol, 77 grams (1 mole) of allylchloride and 50 ml of toluene was stirred under nitrogen until it was homogeneous. There was added to the mixture 24 grams (0.6 mole) of sodium hydroxide and the solution was further heated at 50° C. for 1 hour with stirring and then three grams (9×10³ mole) of tetrabutylammonium bromide was added. After heating the mixture for 16 hours with stirring at 45°-60° C. the mixture was poured into 500 ml of water. The aqueous layer was washed with toluene and the toluene was combined with the organic layer. The organic layer was washed three times with 100 ml portions of water and the dried over anhydrous sodium sulfate. The toluene was then removed under vacuum. There was obtained 59.8 grams or a 93% yield of product. Based on method of preparation, the product a bisallylether of the formula,

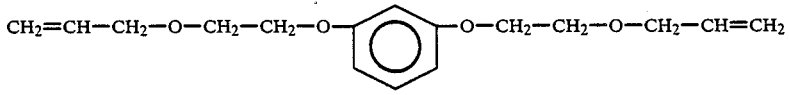

The identity of the above product was further confirmed by NMR.

A mixture of 27.8 grams (0.1 mole) of the above bisallylether of bisethoxylated resorcinol, and 0.24 grams (2×10⁻⁴ mole) of RuCl₂[P(C₆H₅)₃] was heated under nitrogen with stirring at 120°-125° C. for 48 hours. The product was allowed to cool and dissolve in diethylether. The product was then washed with water and the resulting ether layer dried over anhydrous sodium sulfate. The ether was then removed under vacuum. There was obtained a liquid bispropenylether having the formula

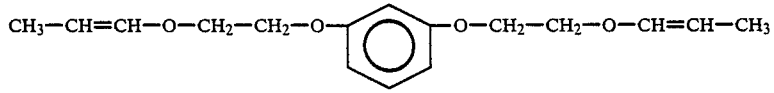

The identity of the above product was further confirmed by NMR.

A UV curable mixture was prepared by combining the above bispropenylether with 1% by weight thereof of diphenyliodonium hexafluorophosphate. A tack-free coating was obtained after a 1 mil film of the mixture was exposed was irradiated for 5 seconds under a GE H3T7 lamp.

EXAMPLE 5

A mixture of 70 grams (0.5 mole) of 1,4-butanediol-monoallylether, 33 grams (0.17 mole) dimethylterephthalate and 0.03 grams of titanium tetraisopropoxide was heated with stirring to a temperature of 180° C. until 4.5 ml of methanol was collected. The reaction mixture was then placed under 0.1 mm pressure and excess 1,4-butanediol-monoallylether was removed by distillation. There was obtained an allylether having the following formula,

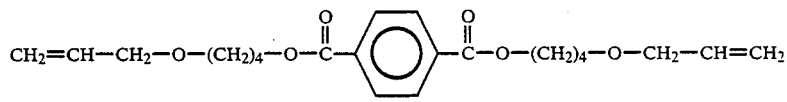

The identity of the above bisallylether was confirmed by NMR analysis.

There was added to 59 grams of the above bisallylether, 0.14 gram (1.5×10⁻⁴ mole) of RuCl₂(PC₆H₅)₃ The resulting mixture was heated and stirred at 120° C. for 2 hours. There was obtained a quantitative yield of a mixture of isomers having the following empirical formula,

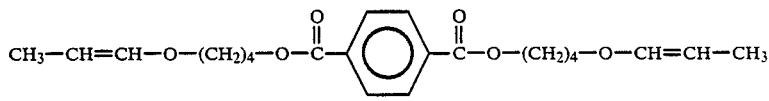

The identity of the above bispropenylether was further confirmed by ¹³C NMR analysis.

A mixture of 9 parts of the above bispropenylether and 1 part of diphenyliodonium hexafluorophosphate was applied as a 1 mil film onto a glass plate. The mixture was then irradiated at a distance of 6 inches from the plate with a GE H3T7 medium pressure mercury arc lamp. A tack-free film was obtained within 1 second.

Although the above examples are directed to only a few of the very many variables which can be used in the practice of the method of the present invention, the method of the present invention can include the use of the aromatic polyallylethers of formula (1) and their isomerization to the corresponding aromatic polypropenylethers of formula (3) as well as the other variables shown in the description preceding these examples.

What we claim as new and desire to secure by Letters Patent of the United States is:

1. A method for making cationically polymerizable polypropenylethers of the formula

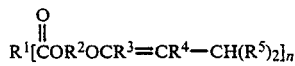

which comprises, (i) effecting reaction between a polyfunctional aromatic ester of the formula

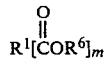

R$^1$[COR$^6$]$_m$ and an allylether of an alkylene glycol of the formula, (R$^5$)$_2$CR$^4$—CH(R$^3$)OR$^2$OH, (ii) heating the aromatic polyallylether of (i) in the presence of an isomerization catalyst selected from the class consisting of metallic palladium, platinum or rhodium on carbon, silicia, or alumina, tris(triphenylphosphone) ruthenium dichloride, [Ir(cyclo-octa-1,5-diene)(PCH$_3$Ph$_2$)$_2$]$^+$PF$_6^-$, PdCl$_2$(PhCN)$_2$, Fe(CO)$_5$, RhCl(PPh$_3$)$_3$, and H$_2$Ru(PPh$_3$)$_4$, where R$^1$ is a polyvalent aromatic radical, R$^2$ is a C$_{(1-8)}$ alkylene radical, R$^3$, R$^4$ and R$^5$ are the same or different monovalent radials selected from hydrogen, halogen and C$_{(1-8)}$ alkyl radicals, R$^6$ is a C$_{(1-8)}$ alkyl radical, n is an integer equal to 2 and 10 inclusive and m is an integer having a value of from 2 to 4 inclusive.

2. A method in accordance with claim 1 in which the cationically polymerizable polypropenylether is

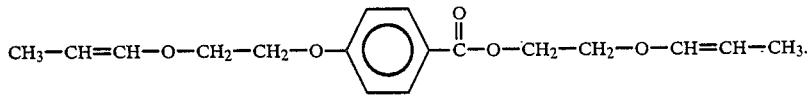

3. A method in accordance with claim 1 in which the cationically polymerizable polypropenylether is

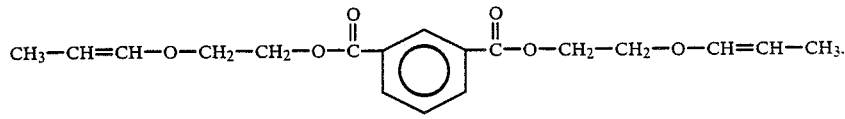

4. A method for making cationically polymerizable polypropenylethers of the formula, R$^1$[OR$^2$OCR$^3$=CR$^4$—CH(R$^5$)$_2$]$_n$ which comprises, (A) effecting reaction between an aromatic polyglycol of the formula R$^1$[OR$^2$OH]$_n$ and an allylhalide in the presence of an acid acceptor to produce an aromatic polyallylether of the formula.

R$^1$[OR$^2$OCHR$^3$—CR$^4$=C(R$^5$)$_2$]$_n$ (B) heating the aromatic polyallylether in the presence of an effective amount of RuCl$_2$(PPh$_3$)$_3$ to produce the desired cationically polymerizable polypropenylether, where R$^1$ is a polyvalent aromatic radical, R$^2$ is a C$_{(1-8)}$ alkylene radical, R$^3$, R$^4$ and R$^5$ are the same or different monovalent radicals selected from hydrogen, halogen and C$_{(1-8)}$ alkyl radicals and n is an integer equal to 2 to 10 inclusive.

* * * * *